(12) United States Patent
Devico et al.

(10) Patent No.: US 6,328,973 B1
(45) Date of Patent: Dec. 11, 2001

(54) METHOD OF RAISING NEUTRALIZING ANTIBODIES AGAINST HIV

(76) Inventors: Anthony L. Devico, 4533 Peacock Ave., Alexandria, VA (US) 22304; Ranajit Pal, 901 Bayridge Ter., Gaithersburg, MD (US) 20878; Mangalasseril G. Sarngadharan, 8422 Holly Leaf Dr., McLean, VA (US) 22101

(*) Notice: Subject to any disclaimer, the term of this patent is extended or adjusted under 35 U.S.C. 154(b) by 0 days.

(21) Appl. No.: 09/479,675

(22) Filed: Jan. 7, 2000

Related U.S. Application Data

(60) Division of application No. 09/075,544, filed on May 11, 1998, now Pat. No. 6,030,772, which is a division of application No. 08/464,680, filed as application No. PCT/US94/05020 on May 6, 1994, now Pat. No. 5,843,454, which is a continuation-in-part of application No. 08/060,926, filed on May 7, 1993, now abandoned.

(51) Int. Cl.[7] .................................................. A01N 65/00
(52) U.S. Cl. .................................. 424/196.11; 424/193.1; 424/194.1; 424/208.1
(58) Field of Search .............................. 424/204.1, 208.1, 424/193.1, 194.1, 195.11, 196.11

(56) References Cited

FOREIGN PATENT DOCUMENTS

| 0385909 | 9/1990 | (EP). |
| WO9205799 | 4/1992 | (WO). |

OTHER PUBLICATIONS

Watanabe, M., Chen, Z.W., Tsubota, H., Lord, C.I., Levine, C.G. and Letvin, N.L. Soluble human CD4 elicits an antibody response in rhesus monkeys that inhibits simian immunodeficiency virus replication. Proc. Natl. Acad. Sci. USA 88:120–124, 1991.

Sattentau, Q.J. and Moore, J.P. Conformational changes induced in the human immunodeficiency virus envelope glycoprotein by soluble CD4 binding. J. Exp. Med. 174:407–415, 1991.

Robert–Guroff, M. HIV–neutralizing antibodies: epitope identification and significance for future vaccine. Int. Rev. Immunol. 7:15–30, 1990.

Putney, S. How antibodies block HIV infection: paths to an AIDS vaccine. TIBS 17:1991–196, 1992.

Putney, S.D., Rusche, J., Javeherian, K., Matthews, T. and Bolognesi, D. Structural and functional features of the HIV envelope glycoprotein and considerations for vaccine development. Biotechnology 14:81–110, 1990.

Allan, J.S., Coligan, J.E., Barin, F., McLane, M.F., Sodroski, J.G., Rosen, C.A., Haseltine, W.A., Lee, T.H. and Essex, M. Major glycoprotein antigens that induce antibodies in AIDS patients are encoded by HTLV–III. Science 228:1091–1094, 1985.

Veronese, F.D., DeVico, A.L., Copeland, T.D., Oroszlan, S., Gallo, R.C. and Sarngadharan, M.G. Characterization of gp41 as the transmembrane protein coded by the HTLV–III/LAV envelope gene. Science 229:1402–1405, 1985.

Ohno, T., Terada, M., Yoneda, Y., Shea, K.W., Chambers, R.F., Stroka, D.M., Nakamura, M. and Kufe, D.W. A broadly neutralizing monoclonal antibody that recognize the V3 region of human immunodeficiency virus type 1 glycoprotein gp120. Proc. Natl. Acad. Sci. USA 88:10726–10729, 1991.

Masuda, T., Matsushita, S., Kuroda, M.J., Kannagi, M., Takatsuki, K. and Harada, S. Generation of neutralization–resistant HIV–1 in vitro due to amino acid interchanges of third hypervariable env region. J. Immunol. 145:3240–3246, 1990.

Ho, D.D., Kaplan, J.C., Rackauskas, I.E. and Gurney, M.E. Second conserved domain of gp120 is important for HIV infectivity and antibody neutralization. Science 239:1021–1023, 1988.

Sun. N.C., Ho, D.D., Sun, C.R., Liou, R.S., Gordon, W., Fung, M.S., Li, X.L., Ting, R.C., Lee, T.H., Chang, N.T. and Chang, T.W. Generation and characterization of monoclonal antibodies to the putative CD4–binding domain of human immunodeficiency virus type 1 gp120. J. Virol. 63:3579–3585, 1989.

Chanh, T.C., Dreesman, G.R., Kanda, P., Linette, G.P., Sparrow, J.T., Ho, D.D. and Kennedy, R.C. Induction of anti–HIV neutralizing antibodies by synthetic peptides. EMBO J. 5:3065–3071, 1986.

Ho, D.D., McKeating, J.A., Li, X.L., Moudgil, T., Daar, E.S., Sun, N.C. and Robinson, J.E. Conformational epitope on gp120 important in CD4 binding and human immunodeficiency virus type 1 neutralization identified by a human monoclonal antibody, J. Virol. 65:489–493, 1991.

Dalgleish, A.G., Beverley, P.C., Clapham, P.R., Crawford, D.H., Greaves, M.F. and Weiss, R.A. The CD4 (T4) antigen is an essential component of the receptor for the AIDS retrovirus. Nature 312:763–767, 1984.

McDougal, J.S., Kennedy, M.S., Sligh, J.M., Cort, S.P., Mawle, A. and Nicholson, J.K. Binding of HTLV–III/LAV to T4 T cells by a complex of the 110K viral protein and the T4 molecule. Science 231:382–385, 1986.

Thali, M., Furman, C., Ho, D.D., Robinson, J., Tilley, S., Pinter, A., and Sodroski, J. Discontinuous, conserved neutralization of epitopes overlapping the CD4–binding region of human immunodeficiency virus type 1 gp120 envelope glycoprotein. J. Virol. 66:5635–5641, 1992.

Moore, J.P., McKeating, J.A., Weiss, R.A. and Sattentau, Q.J. Dissociation of gp120 from HIV–1 virus induced by soluble CD4. Science 250:1139–1142, 1990.

(List continued on next page.)

*Primary Examiner*—Jeffrey Stucker

(57) ABSTRACT

The present invention is directed to a method of raising neutralizing antibodies against HIV using a complex of gp120 covalently bonded to CD4 or a complex of gp120 covalently bonded to succinyl concanavalin A.

2 Claims, 6 Drawing Sheets

OTHER PUBLICATIONS

Hart, T.K., Kirsh, R., Ellens, H., Sweet, R.W., Lambert, D.M. Petteway, S.R.,Jr., Leary, J. and Bugelski, P.J. Binding of soluble CD4 proteins to human immunodeficiency virus type 1 and infected cells induces release of envelope glycoprotein gp120. Proc. Natl. Acad. Sci. USA 88:2189–2193, 1991.

Mizuochi, T., Matthews, T.J., Kato, M., Hamako, J., Titani, K., Solomon, J. and Feizi, T. Diversity of oligosaccharide structures on the envelope glycoprotein gp 120 of human immunodeficiency virus 1 from the lymphoblastoid cell line H9. Presence fo complex–type oligosaccharides with bisecting N–acetylglucosamine residues. J. Biol. Chem. 265:8519–8524, 1990.

Geyer, H., Holschbach, C., Hunsman, G. and Schneider, J. Carbohydrates of human immunodeficiency virus. Structures of oligosaccharides linked to the envelope glycoprotein 120. J. Biol. Chem. 263:11760–11767, 1988.

Larkin, M., Childs, R.A., Matthews, T.J., Thiel, S., Mizuochi, T., Lawson, A.M., Savill, J.S., Haslett, C., Diaz, R. and Feizi, T. Oligosaccharide–mediated interactions of the envelope glycoprotein gp120 of HIV–1 that are independent of CD4 recognition. AIDS 3:793–798, 1989.

Ezekowitz, R.A., Kuhlman, M., Groopman, J.E. and Byrn, R.A. A human serum mannose–binding protein inhibits in vitro infection by the human immunodeficiency virus. J. Exp. Med. 169:185–196, 1989.

Schooley, R.T., Merigan, T.C., Gaut, P., Hirsch, M.S., Holodniy, M., Flynn, T., Liu, S., Byington, R.E., Henochowicz, S., Gubish, E. and et al., Recombinant soluble CD4 therapy in patients with the acquired immunodeficiency syndrome (AIDS) and AIDS–related complex. A phase I–II escalating dosage trial. Ann. Intern. Med. 112:247–253, 1990.

Watanabe, M.,Boyson, J.E., Lord, C.I. and Letvin, N.L. Chimpanzees immunized with recombinant soluble CD4 develop anti–self CD4 antibody responses with anti–human imunodeficiency virus activity. Proc. Natl. Acad. Sci. USA 89:5103–5107, 1992.

Kahn, J.O., Allan, J.D., Hodges, T.L., Kaplan, L.D., Arri, C.J., Fitch, H.F., Izu, A.E., Mordenti, J., Sherwin, J.E., Groopman, J.E. and et al, The safety and pharmacokinetics of recombinant soluble CD4 (rCD4) in subjects with the acquired immunodeficiency syndrome (AIDS) and AIDS–related complex. A phase 1 study. Ann. Intern. Med. 112:254–261, 1990.

Grewe, C., Beck, A., and Gelderblom, H.R. HIV: Early virus–cell interactions. J. Acq. Immune Def. Synd. 3:965–974, 1990.

Robinson, W.E., Jr., Montefiori, D.C. and Mitchell, W.M. Evidence that mannos yl residues are involved in human immunodeficiency virus type 1 (HIV–1) pathogenesis. AIDS Res. Hum. Retroviruses 3:265–282, 1987.

Cattegno, L., Ramdani, A., Jouault, T., Saffar, L. and Gluckman, J.C. Lectin–carbohydrate interactions and infectivity of human immunodeficiency virus type 1 (HIV–1). AIDS Res. Hum. Retroviruses 8:27–37, 1992.

Pal, R., Veronese, F.D., Nair, B.C., Rahman, R., Hoke, G., Mumbauer, S.W., and Sarngadharan, M.G. Characterization of a neutralizing monoclonal antibody to the external glycoprotein of HIV–1. Intervirology, in press.

Veronese, F.D., Rahman, R., Pal, R., Boyer, C., Romano, J., Kalyanaraman, V.S., Nair, B.C., Gallo, R.C. and Sarngadharan, M.G. Delineation of immunodeficiency virus type 1. AIDS Res. Human Retroviruses 8:1125–1132, 1992.

Celada, F., Cambiaggi, C., Maccari, J., Burastero, S., Gregory, T., Patzer, E., Porter, J., McDanal, C. and Matthews, T. Antibody Raised against Soluble CD4 rgp120 complex recognizes the CD4 moiety and blocks membrane fusion without inhibiting CD4–gp120 binding. J. Exp. Med., 172:1143–1150, 1990.

B.F. Haynes, Science, 260:1279–1286, May 28, 1993.

W.G. Robey et al., Proc. Natl. Acad. Sci. USA, 83:7023–7027, Sep. 1986.

S.M. Chamov et al., Journal of Biological Chemistry, 267(22):15916–15922, 1992.

J. Cohen, Science, 262:980–981, Nov. 12, 1993.

O.J. Sattentau et al., J. Exp. Med., 174:407–415, Aug. 1991.

C. Kang et al., FASEB Journal, 8:5:Abstract 5567, Apr. 1994.

J.M. Gershoni et al., FASEB Journal, 7:12:1185–1187, Sep. 1993.

R. Pal et al., Virology, 194:833–837 (1993).

Edelman et al., International Review of Immunology, 7:1:51–66, 1990.

METHOD OF RAISING NEUTRALIZING ANTIBODIES AGAINST HIV

CROSS-REFERENCE TO RELATED APPLICATIONS

The present application is a divisional of U.S. application Ser. No. 09/075,544 filed on May 11, 1998, now U.S. Pat. No. 6,030,772, which is a divisional of U.S. application Ser. No. 08/464,680 filed on Dec. 20, 1995, now U.S. Pat. No. 5,843,454, which is a national phase filing of PCT/US94/05020 filed on May 6, 1994, which is a continuation-in-part of U.S. application Ser. No. 08/060,926, now abandoned.

DESCRIPTION OF THE INVENTION

We discovered that a gp120-CD4 covalently bonded complex presents a specific subset of cryptic epitopes on gp120 and/or CD4 not present on the uncomplexed molecules. These complexes elicited neutralizing antibodies with novel specificities and are thus useful in vaccines and immunotherapy against HIV infection. In addition, the complexes or antibodies thereto can be used in immunological tests for HIV infection.

BACKGROUND OF THE INVENTION

Neutralizing antibodies are considered to be essential for protection against many viral infections including those caused by retroviruses. Since the initial reports of neutralizing antibodies in HIV-infected individuals, it has become increasingly clear that high levels of these antibodies in serum correlate with better clinical outcome (3–5). These studies suggested that the identification of epitopes that elicit high titer neutralizing antibodies would be essential for vaccine development against HIV infection.

The primary receptor for the human immunodeficiency virus type 1 (HIV-1) is the CD4 molecule, found predominantly on the surface of T-lymphocytes. The binding of HIV-1 to CD4 occurs via the major viral envelope glycoprotein gp120 and initiates the viral infection process.

Current strategies for developing vaccines against infection by the human immunodeficiency virus have focused on eliciting antibodies against the viral envelope glycoprotein gp120 or its cell surface receptor CD4. Purified gp120 typically elicits type specific neutralizing antibodies that are reactive against epitopes that vary among virus isolates. This characteristic has hindered the use of gp120 as a vaccine.

CD4 has also been considered as a major candidate for development of a vaccine against HIV-1. Recent studies have demonstrated that sCD4 elicits HIV neutralizing antibodies in animals and prevents the spread of infection in SIV-infected rhesus monkeys (1). However, autoantibodies to CD4 may themselves create immune abnormalities in the immunized host if they interfere with normal T-cell functions. Neutralizing antibodies against gp120 are elicited in vivo in HIV-1-infected individuals and can be elicited in vitro using purified envelope glycoprotein. However, gp120 contains five hypervariable regions one of which, the V3 domain, is the principal neutralizing epitope. Hypervariability of this epitope among strains is a major obstacle for the generation of neutralizing antibodies effective against diverse strains of HIV-1. For these reasons it has been believed that vaccine strategies using either purified CD4 or gp120 present several disadvantages.

We have overcome the shortcomings of type specific anti gp120 antibodies and antibodies against CD4 by raising anti-HIV-1 neutralizing antibodies using as the immunogen a complex of gp120 chemically coupled to either soluble CD4 or to the mannose-specific lectin, succinyl concanavalin A (SC). We have found that these compounds induce similar conformational changes in gp120. The complexed gp120 appears to undergo a conformational change that presents an array of epitopes that were hidden on the uncomplexed glycoprotein (2). A portion of such epitopes elicit group-specific neutralizing antibodies, which are not strain limited like the type specific antibodies discussed above. We have discovered that the covalently bonded CD4-gp120 complexes are useful for raising neutralizing antibodies against various isolates of HIV-1 and against HIV-2.

The major research effort in the development of subunit vaccines against HIV has been directed toward the envelope glycoprotein of the virus. Inoculation of gp160 or gp120 into animals elicits neutralizing antibodies against HIV (3, 4). The principal neutralizing epitope on gp120 has been located between amino acids 306 and 326 in the third variable domain (V3 loop) of the protein (4). This epitope has been extensively studied by using both polyclonal and monoclonal antibodies (3, 4) In most cases antibodies directed to this region neutralize HIV-1 in an isolate specific manner although there is evidence that a weakly neutralizing species of anti-V3 loop antibodies can cross-react with diverse isolates (8). The reason for type specificity of anti-V3 loop antibodies is the extensive sequence variability among various isolates. Prolonged culturing of HIV-infected cells with type specific anti-V3 loop antibodies induces escape mutants resistant to neutralization (9).

In addition to the V3 loop, other neutralizing epicopes encompassing genetically conserved regions of the envelope have been identified (10, 11). However, immunization against these epitopes elicits polyclonal antisera with low neutralizing titers (12). For example, the CD4 binding region of gp120, encompassing a conserved region, elicits neutralizing antibodies against diverse isolates (13). However, this region is not normally an immunodominant epitope on the glycoprotein.

The interaction of gp120 with CD4 has been studied in considerable detail and regions of the molecules involved in complex formation have been determined (14–16). There are now several lines of evidence that interactions with CD4 induce conformational changes in gp120. First, recombinant soluble CD4 (sCD4) binding to gp120 increases the susceptibility of the V3 loop to monoclonal antibody binding and to digestion by exogenous proteinase (2). Second, sCD4 binding results in the dissociation of gp120 from the virus (17, 18). These conformational changes in gp120 are thought to facilitate the processes of virus attachment and fusion with the host cell membrane (2). Immunization with soluble CD4 and recombinant gp120, complexed by their natural affinity but not covalently bonded, resulted in the production of anti CD4 antibodies (31). Several murine monoclonal antibodies have been developed by immunization with mixtures of recombinant gp120 and sCD4 (31, 32). Antibodies raised in these studies were not strictly complex-specific and reacted with free gp120 or CD4; the neutralizing antibodies reacted with free sCD4, although they displayed various degrees of enhanced reactivity in the presence of gp120. The complexes used in these studies were unstable and comprised noncovalently bound gp120 and CD4.

A variety of N-linked carbohydrate structures of high mannose, complex and hybrid types present on the gp120 molecule may also play a role in the interaction of gp120 with host cell membranes (19–21). Indeed, a carbohydrate-mediated reactivity of gp120 has already been demonstrated with a serum lectin, known as mannose-binding protein, which has also been shown to inhibit HIV-1 infection of CD4+cells (22). An additional carbohydrate-mediated interaction of gp120 has been shown with the endocytosis receptor of human macrophage membranes (21). It has been postulated that high affinity binding of accessible mannose residues on gp120 to the macrophage membrane may lead to virus uptake by the macrophage (21).

Recombinant soluble CD4 has been shown to inhibit HIV infection in vitro, mainly by competing with cell surface CD4. This observation has led to the possibility of using sCD4 for the therapy of HIV-infected individuals (23, 24). In addition, sCD4 has been used as an immunogen to block viral infection in animals. Treatment of $SIV_{mac}$-infected rhesus monkeys with sCD4 elicited not only an antibody response to human CD4 but also to monkey CD4. Coincident with the generation of such immunological responses, SIV could not be isolated from the PBL and bone marrow macrophages of these animals (1). A recent study with chimpanzees also demonstrated that human CD4 elicited anti-self CD4 antibody that inhibited HIV infection in vitro (25). Although immunization with sCD4 may be beneficial in blocking HIV infection, circulating antibody that recognizes self antigen may induce immune abnormality and dysfunction by binding to uninfected CD4+cells. Nevertheless in theory anti-CD4 antibodies could be effective in blocking HIV infection provided they can disrupt virus attachment and entry without interfering with normal CD4 function. Ideally these antibodies should recognize CD4 epitopes that are present only after interaction with gp120.

SUMMARY OF THE INVENTION

We discovered that gp120-CD4 complex formation induces a specific subset of cryptic epitopes on gp120 and/or CD4 not present on the uncomplexed molecules. These epitopes elicit neutralizing antibodies with novel specificities and are thus useful in vaccines and/or immunotherapy of patients infected with HIV. In addition, the antibodies or the complexes can be used in immunological tests for HIV infection. We have demonstrated that the lectin, SC, mediates changes in the structure of gp120 in a manner similar to that mediated by CD4. The binding of SC to gp120 is another mechanism for inducing novel epitopes on the viral glycoprotein.

We used chemically-coupled gp120-CD4 complexes as immunogens for raising neutralizing antibodies. We found that gp120-CD4 complexes possess novel epitopes that elicit neutralizing antibodies. Coupling with SC caused perturbation in the gp120 conformation which in turn unmasked cryptic neutralizing epitopes on gp120.

DESCRIPTION OF THE FIGURES

FIG. 1 shows the dissociation of gp120 from HIV-1 in the presence of sCD4 and SC.

FIG. 2 illustrates the susceptibility of gp120 to thrombin digestion in the presence of SC and sCD4. Molt3/HIV-1$_{IIIB}$ cells were labeled with $^{35}$S-methionine for 4 hr, followed by a 3 hr incubation with medium containing 0.25% methionine.

FIG. 3 shows the inhibition of HIV-1 induced syncytia formation by murine antisera raised against gp120-sCD4.

FIG. 4 lane 1 is gp120, lane 2 is sCD4, Lane 3 has a gp120-CD4 complex and lane 4 has molecular weight markers.

DETAILED DESCRIPTION OF THE EMBODIMENTS

Figure 1A:
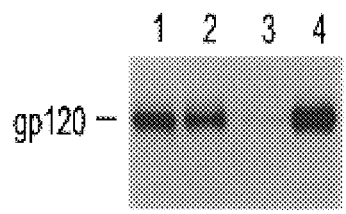
In FIG. 1A labeled cells were treated with 0 (lanes 1, 2) or 1.5 μg/ml sCD4 (lanes 3, 4). Virus bound (lanes 1, 3) or soluble (lanes 2, 4) gp120 was detected by immunoprecipitation with HIV-1 antibody-positive human serum, SDS-PAGE and autoradiography.

We determined that it was necessary to unmask or create new epitopes on gp120 and/or CD4 capable of eliciting a strong, broadly neutralizing immune response. We used a covalently linked gp120-CD4 complex as an immunogen. gp120 molecules were covalently coupled to soluble recombinant CD4 using bivalent cross-linking agents to ensure that the integrity of the complexes was maintained during any manipulations. The components of the complex were expected to differ from the free glycoprotein in at least two ways: (I) some epitopes on gp120 and CD4 would be masked by complex formation and (II) cryptic epitopes would become exposed as a result of conformational changes in gp120 and CD4 of the complex. Because these epitopes could play a significant role in viral entry into target cells, antibodies directed against them should inhibit some aspects of the entry process. We believed these antibodies may not inhibit gp120-CD4 interaction but may instead prevent post-binding fusion events necessary for infection.

The application of this strategy toward anti-HIV vaccines offered several other advantages. First, epitopes specific to complexed gp120 are not expected to be normal targets for neutralizing antibodies in vivo. HIV-1 binds and enters target cells within 3 min at 37° C. (26). Given the transient and short-lived nature of the native gp120-CD4 complex, it is unlikely that it is presented to the immune system in such a way as to elicit complex-specific antibodies. Therefore, the absence of immune selection in vivo should in turn be reflected in a minimal degree of variation in the complex-specific epitopes of different viral strains. Second, antibodies against complex-specific epitopes on CD4 are not expected to elicit anti-self antibodies capable of recognizing uncomplexed CD4 on the surface of normal cells. This is especially important, since anti-CD4 antibodies can mediate cytotoxic effects.

In the development of vaccines against HIV, the ability to induce novel epitopes on gp120 in the absence of CD4 would be of considerable advantage. We discovered this is possible. We have bound a mannose-specific lectin, SC, with gp120, which induces a conformational change on the glycoprotein that appears to be similar to that observed with sCD4. The alterations include exposure of the V3 loop to exogenous protease and dissociation of gp120 from the virus membrane. Therefore, covalently linked gp120-SC complexes are also useful as immunogens for exposing novel epitopes and complex specific antibodies in the absence of CD4.

The vaccines of the present invention are composed of the complex of gp120-CD4 or gp120-SC together with an acceptable suspension known in the vaccine art. Preferably, an adjuvant may be added. The only adjuvant acceptable for use in human vaccines is aluminum phosphate (alum adjuvant), and therefore preferably the vaccine of the present invention is formulated with an aluminum phosphate gel. See Dolin et al., *Ann Intern Med,* 1991;114:119–27, which is incorporated herein by reference. The dose of the immunogenic complex for purposes of vaccination is between about 40 $\mu$g to about 200 $\mu$g per inoculation. An initial inoculation may be followed by one or more booster inoculations. Preferably, the vaccination protocol will be the same as protocols now used in clinical vaccination studies and disclosed in Dolin et al., supra, and Reuben et al.,*J Acquired Immune Deficiency Syndrome,* 1992;5:719–725, also incorporated herein by reference.

It is also contemplated that antibodies raised against the immunogenic complexes of the present invention can be used for passive immunization or immunotherapy. The dosage and number of inoculations of these antibodies will follow those established in the art for immunization or immunotherapy with immunoglobulins.

The complexes or antibodies thereto can also be used in a method for the detection of HIV infection. For instance, the complex, which is bound to a solid substrate or labelled, is contacted with the test fluid and immune complexes formed between the complex of the present invention and antibodies in the test fluid are detected Preferably, antibodies raised against the immunogenic complexes of the present invention are used in a method for the detection of HIV infection. These antibodies may be bound to a solid support or labelled in accordance with known methods in the art. The detection method would comprise contacting the test fluid with the antibody and immune complexes formed between the antibody and antigen in the test fluid are detected and from this the presence of HIV infection is determined. The immunochemical reaction which takes place using these detection methods is preferably a sandwich reaction, an agglutination reaction, a competition reaction or an inhibition reaction.

A test kit for performing the methods mentioned in the preceding paragraph must contain either the immunogenic complex according to the present invention or one or more antibodies raised thereto. In the kit, the immunogenic complex or the antibody(ies) are either bound to a solid substrate or are labelled with conventional labels. Solid substrates and labels, as well as specific immunological testing methods are disclosed in Harlow and Lane, "Antibodies, A Laboratory Manual", Cold Spring Harbor Laboratory, 1988, incorporated herein by reference.

EXAMPLES

We conducted several studies to show that new epitopes could be exposed on gp120 and CD4. These studies also demonstrated that neutralizing antibodies could be raised against gp120 after treatment that altered the conformation of the glycoprotein.

Example I a. Conformational Changes in gp120 Induced By Complex Formation With CD4:

We analyzed the release of gp120 from the virus surface under various conditions. Molt3/HIV-1$_{IIIB}$ cells were labeled with 35S-methionine (150 $\mu$Ci/ml) for 3 hours. The labeled cells were then washed and resuspended in RPMI medium containing cold methionine. The cells were then cultured for 4 hours in the presence of recombinant sCD4 (DuPont). The cell-free supernatant was collected and then passed through a Sephacryl S 1000 column in order to separate virions from free viral proteins. Each of the fractions was treated with detergent, immunoprecipitated with human sera positive for anti-HIV-1 antibodies, and analyzed by SDS-PAGE and autoradiography. The amount of gp120 present in the virus and free viral protein fractions was quantitated by a densitometric scan of the autoradiograph. In accordance with previous studies (17, 18), we observed that treatment of virus with sCD4 clearly resulted in an increased level of gp120 in the free protein fraction and a coincident decrease in the virus fraction (FIG. 1A). indicating that the conformation of gp120 was altered to dissociate it from the virion.

Figure 1B:
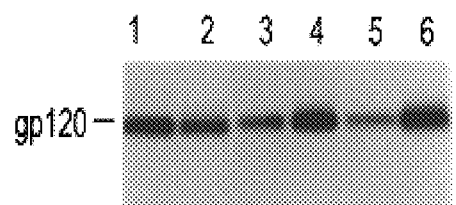
In FIG. 1B labeled cells were treated with 0 (lanes 1, 2), 5 μg/ml (lanes 3, 4) or 10 μg/ml SC (lanes 5, 6). Virus bound (lanes 1, 3, 5) or soluble (lanes 2, 4, 6) gp120 was detected as in 1A.
Figure 2A:
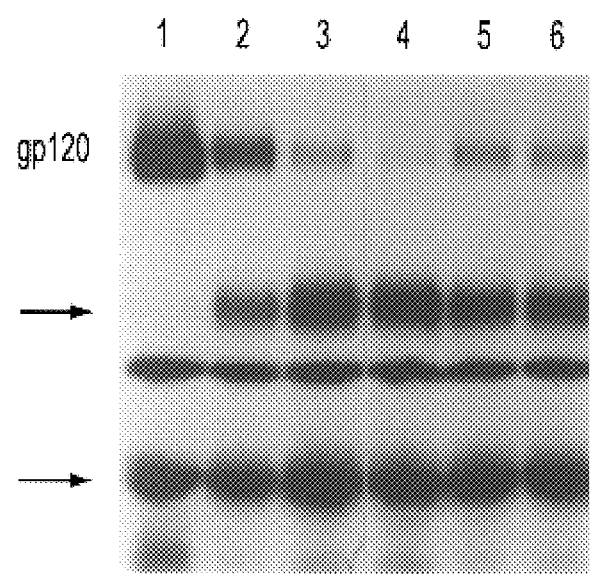
In FIG. 2A an aliquot of labeled medium (1 ml) was digested with thrombin (7 μg/ml) at 37° C. for 90 min and then immunoprecipitated with HIV-1 positive human serum and analyzed by SDS-PAGE. Lane 1 shows untreated medium and lane 2, medium treated with thrombin. Prior to thrombin digestion, aliquots of the medium were pretreated with SC at concentrations of 2.5 μg/ml (lane 3), or 10 μg/ml (lane 4); or with sCD4 at concentrations of 2.5 μg/ml (lane 5) or 10 μg/ml (lane 6). The gp120 fragments generated by thrombin cleavage are marked with arrows.
Figure 2B:
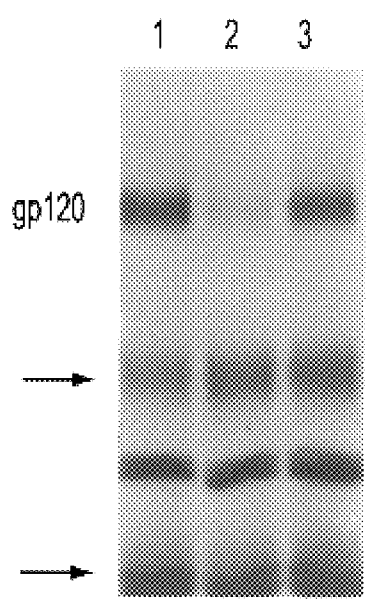
In FIG. 2B aliquots of labeled medium were digested by thrombin as before with no pretreatment (lane 1), after pretreatment with 5 μg/ml SC (lane 2 or with a mixture of 5 μg/ml SC and 0.1 mM α-methylpyranoside (lane 3).

To further investigate how sCD4 alters the conformation of gp120, we conducted studies on thrombin-mediated cleavage of gp120. Digestion of gp120 by thrombin generates 70 kD and 50 kD products (FIG. 2A). This cleavage takes place at the V3 loop. A monoclonal antibody directed against an epitope within the loop blocks the cleavage completely. The thrombin-mediated cleavage at the V3 loop of gp120 is enhanced after binding with sCD4. This indicates an increased exposure of the V3 loop on the surface of the protein, which renders it more susceptible to protease cleavage.

b. Conformational Changes In gp120 Induced By Complex Formation With Succinyl Concanavalin A It was previously demonstrated that the incubation of HIV with mannose-specific lectins, such as concanavalin A or succinyl concanavalin A attenuates viral infectivity (27, 28). Incubation of 35S-methionine-labeled gp120 with SC resulted in the enhanced susceptibility of the V3 loop to thrombin digestion (FIG. 2A) This effect was specific, as preincubation of lectin with a-methyl mannoside blocked the enhanced effect completely (FIG. 2B). In addition to increasing the exposure of the V3 loop, interaction of HIV-1 with SC resulted in a dissociation of gp120 from the viral membrane (FIG. 1B). The degree of such shedding was somewhat less than that observed with sCD4. Nevertheless, these studies clearly indicated that sCD4 and SC alter the conformation of gp120, and in a very similar manner.

c. Immunological Properties Of Chemically Coupled gp120-CD4 Complexes

Figure 3A:
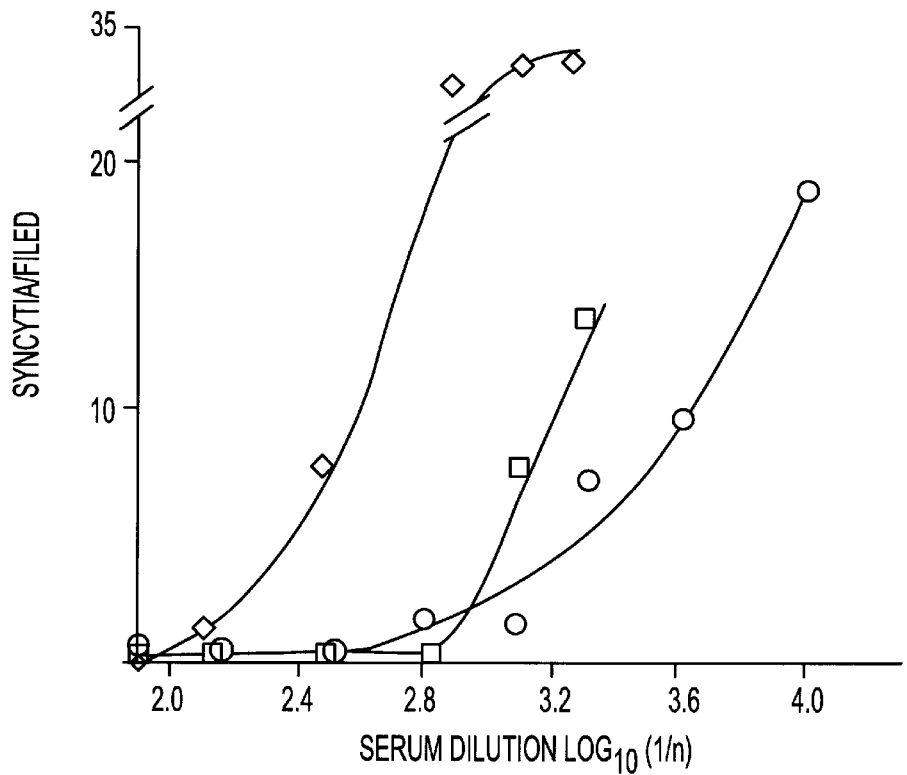
In FIG. 3A murine antiserum raised against gp120-sCD4 was added to CEM cells along with cells infected with HIV-1$_{IIIB}$ (○), HIV-1$_{MN}$ (□) or HIV-2$_{WAVZ}$ (◇).

We demonstrated that gp120-sCD4 complexes are immunogenic and capable of eliciting HIV-1-neutralizing antibodies. An immunoaffinity procedure was used to purify gp120 from chronically-infected H9/HIV-1$_{IIIB}$ cells. The purified gp120 was then crosslinked to sCD4 (DuPont) using the noncleavable, water-soluble crosslinker, bis (sulfosuccinimidyl) suberate (BS). Mice were inoculated with the complexes and the immune sera examined for any effect on HIV-induced syncytium formation. Syncytium formation induced by HIV-1$_{IIIB}$ and HIV-1$_{MN}$ infected cells was markedly inhibited by the immune sera. A representative inhibition curve of one immune serum is shown in FIG. 3A. Syncytium formation induced by cells infected with the highly related HIV-2 was also inhibited in the presence of the serum. These results demonstrate that gp120-sCD4 complexes are capable of eliciting broadly neutralizing antisera.

Figure 3B:
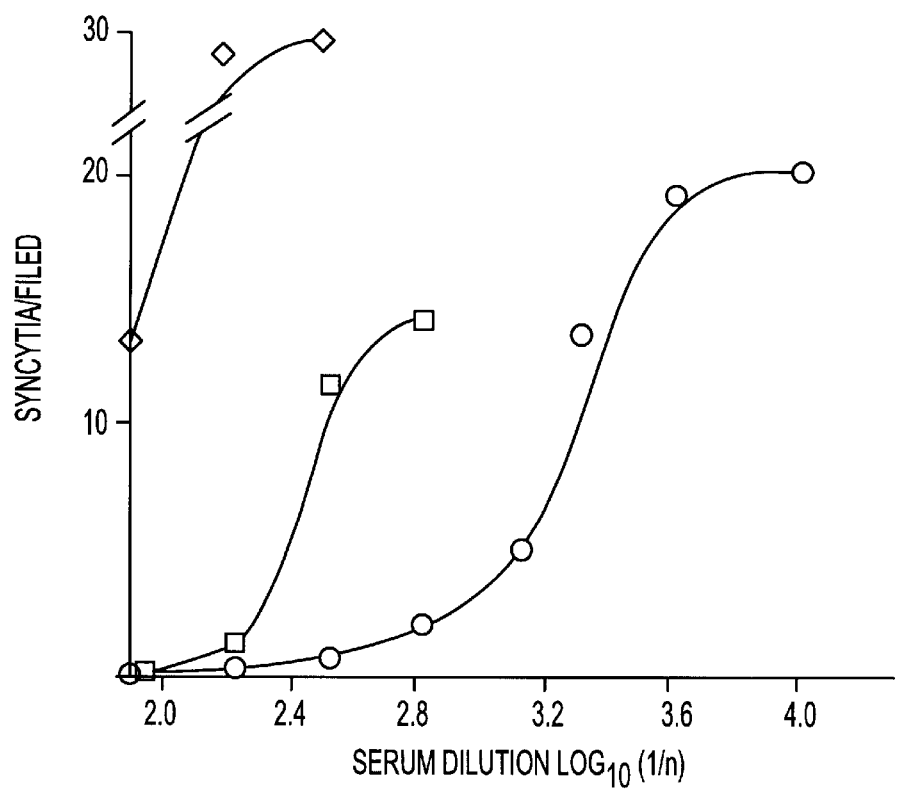
In FIG. 3B murine antisera raised against thrombin treated gp120-sCD4 complexes were tested. The assay conditions are described in the Examples. For each experimental condition, the syncytia in three separate fields were counted. The average value is given as syncytia/field.

We also inoculated mice with complexes comprised of thrombin-digested gp120 and sCD4. In this case, the gp120 V3 loop was expected to be modified by protease cleavage. Since V3 has been reported to be the neutralizing epitope on gp120, it has been of interest to determine how such cleavage would affect the ability of the complex to elicit neutralizing antibodies. As shown in FIG. 3B, inoculation of mice with thrombin-digested gp120-CD4 complexes elicited antibody capable of blocking syncytium formation induced by the HIV-1$_{IIIB}$ and HIV-1 isolates. However, this inhibiting effect was not observed with HIV-2 induced syncytium formation.

Our preliminary experiments clearly demonstrated that the covalently coupled gp120-CD4 complexes can elicit a broadly neutralizing antibody response. We then undertook to determine whether cryptic epitopes on the complex are recognized by the neutralizing antibodies and to characterize the epitopes.

Example II
Immunological Properties of gp120-CD4 Complex

The glycoprotein gp120 used in the preparation of gp120-CD4 complex was purified from H9/HIV-1$_{IIIB}$ cells by immunoaffinity chromatography. The cells were lysed in a buffer containing 20 mM Tris (pH 8.2), 0.15 M NaCl, 1.0% Triton X-100, and 0.1 mM PMSF. The lysate was centrifuged at 100,000×g for 1 hr. The NaCl concentration in the supernatant was adjusted to 1 M and the lysate was then reacted with an affinity matrix prepared with human anti-HIV immunoglobulins purified from serum of an HIV-antibody positive subject. The bound antigens were eluted with 50 mM diethylamine, pH 11.5, and the pH of the eluate was immediately adjusted to 8.0 with Tris HCl. The eluate was extensively dialyzed against 10 mM phosphate buffer (pH 6.5) containing 0.5 M NaCl, 0.1 mM CaCl$_2$, 1 mM MgCl$_2$, and 0.2 mM MnCl$_2$, followed by the addition of Triton X-100 to reach 0.2% by weight solution of the detergent. The dialyzed material was then passed through a lentil-lectin column. The glycoproteins were isolated from the lentil-lectin column by elution with 0.4 M α-methylmannoside and were then dialyzed against 20 mM Tris HCl (pH 8.2) containing 1 M NaCl and 0.2% Triton X-100. The dialyzed material was then applied to an affinity matrix prepared with a mouse monoclonal antibody SVM-25 (U.S. Pat. No. 4,843,011) reactive against gp41 to absorb gp160 and any gp41 present. The flow-through from the affinity column was dialyzed extensively against 10 mM BES (pH 6.5) containing 1 mM EDTA and was loaded on a phosphocellulose column equilibrated with the same buffer. The column was developed with a linear gradient of 0–500 mM NaCl and fractions containing gp120 were pooled, concentrated, and dialyzed against PBS.

The purified glycoprotein was coupled to sCD4 (commercially obtained from dupont) by using bis (sulfosuccinimidyl) suberate (BS) (Pierce) as a crosslinker. For this gp120 and sCD4 were mixed at 1:2 molar ratio in PBS and incubated at 37° C. for 1 hr followed by treatment with 0.5 mM BS at room temperature for 1 hr. The complex was further incubated overnight at 4° C. The excess BS was blocked with 20 mM Tris-HCl (pH 8.0).

Development of gp120-CD4 Complex-Specific Monoclonal Antibodies

Balb/C mice were subjected to six biweekly inoculations of the gp120-CD4 complex. The initial inoculum (48 kg per mouse) was emulsified in Complete Freunds Adjuvant and administered by subcutaneous injection. In subsequent inocula (24 µg/mouse) were emulsified in Incomplete Freunds Adjuvant and were administered by intraperitoneal injection. Two weeks after the final inoculation the animals were bled and the sera examined for HIV-1 neutralizing antibodies by a syncytium blocking assay. Briefly, CEM cells (1×10$^5$) were counted with HIV-1-infected cells (1×10$^4$) in the presence of the test serum and the number of giant cells were counted after 24–40 hr Syncytium formation induced by HIV-1$_{IIIB}$- and HIV-1$_{MN}$-infected cells was markedly inhibited by the serum of the mice that was immunized with gp120-CD4 complex. Syncytium formation induced by HIV-2-infected cells was also inhibited by these sera indicating that gp120-CD4 complexes are capable of eliciting broadly neutralizing antibodies in mice.

After detection of neutralizing antibodies in mice, the animals received a final intraperitoneal form of gp120-CD4 complex in PBS without adjuvant. On the fourth day, the animals were sacrificed and the spleen extracted. Splenic lymphocytes were flushed from the spleen with a syringe. The cells (7×10$^7$) were fused with 1×10$^7$ NS-1 mouse myeloma cells (ATCC, Rockville, Md.), overnight in super HT [DMEM containing 20% fetal calf serum (Hyclone), 0.1 M glutamine, 10% NCTC-$^{109}$ lymphocyte conditioned medium, 0.5 mM Na-pyruvate, 0.2 U/ml insulin, 1 mM oxalacetic acid, and 100 U/ml penicillin/streptomycin] (GIBCO) containing 40% PEG 1540. The cells are then suspended in super HT containing 0.4 µM aminopterin and placed in 96-well plates.

Initially, hybridomas were selected for the production of gp120-CD4 complex-specific antibodies. Pooled hybridoma supernatants were tested in the ELISA using gp120, CD4 and gp120-CD4 as antigens. Supernatants of pools containing complex-specific antibodies were tested individually. Hybridomas of interest were cloned by replating in super HT at a density of 1 cell/well. Supernatants from cloned hybridomas were further tested by ELISA using gp120-CD4 complexes.

Four hybridomas were selected which secreted immunoglobulin demonstrating a high level reactivity against gp120-CD4 complex and negligible reactivity with either gp120 or sCD4 in ELISA (Table 1). Notably, one of the monoclonal antibodies, MoAb 7E3, was of the IgA isotype. Immunoglobulins were subsequently purified from the ascites fluid of each hybridoma and further analyzed by Western blot assay with gp120-CD4 complexes, free gp120, or sCD4. While none of the antibodies reacted with free gp120 or sCD4, antibodies 7E3 and 8F10B displayed high levels of reactivity with the complex (FIG. 4) and a low molecular weight fragment of complex. Although antibodies 8F10C and 8F10D reacted strongly with the complex in ELISA (Table 1), reactivity with the complex in Western blot was weak. These results suggest that MoAbs 8F10C and 8F10D are directed against a set of highly conformation-dependent, complex-specific epitopes that are distinct from the epitopes recognized by MoAbs 7E3 and 8F10B.

Purified 7E3, 8F10B, 8F10C, and 8F10D immunoglobulins were tested in cell-free infection assays using PHA-stimulated peripheral blood mononuclear cells (PBMCs) and a variety of HIV-1 isolates. As shown in Table 2, none of the antibodies had any significant effect on the infection of PBMC by the laboratory-adapted strain, HIV-1$_{IIIB}$. However, antibodies 7E3, 8F10B, and 8F10C neutralized the infection of PBMC by a primary isolate of HIV-1MN to a significant extent, whereas antibody 8F10D had no effect. In contrast to these results, none of the antibodies blocked syncytium formation induced by H9/HIV-1$_{IIIB}$ or H9/HIV-1MN on CEM cells. Our preliminary experiments suggest that the extent of cell-free neutralization by these complex-specific antibodies may depend on the infection rate of the isolate. In general, primary HIV-1 strains with lower infection rates tend to be neutralized more effectively than more virulent lab-adapted strains of HIV-1.

Figure 5:
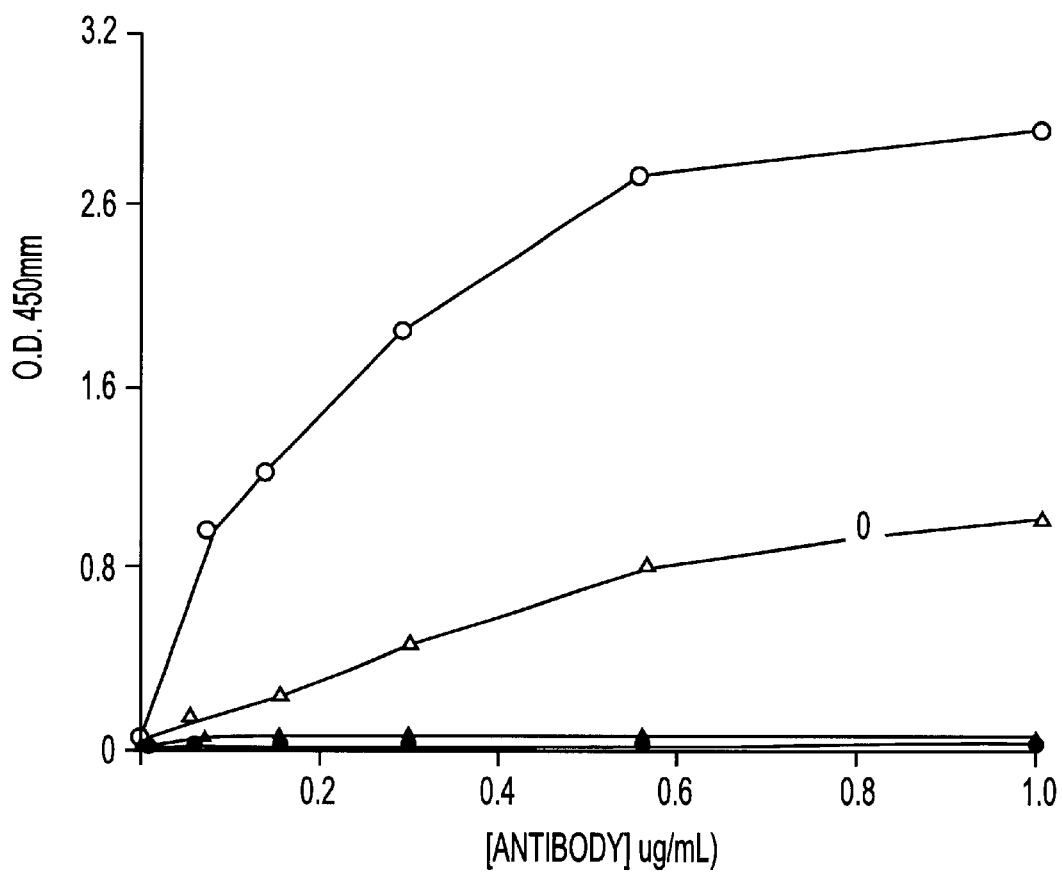
FIG. 5 is a graph showing the binding of complex-specific monoclonal antibodies to gp120-lectin complex. MoAbs A(○) and B(△) were tested in ELISA, with either gp120-SC (open symbols) or gp120 (closed symbols).

To determine whether the complex-specific antibodies bind to the gp120 or the CD4 moiety of the complex, we took advantage of our demonstration that the mannose-specific lectin, succinyl conA (SC), perturbs the conformation of the glycoprotein in a manner similar to that induced by sCD4 (33). SC and gp120 were cross-linked with BS3 and tested in ELISA. MoAbs 7E3 and 8F10B reacted strongly with the gp120-SC complex (FIG. 5) but did not react with free gp120 or SC. In contrast, antibodies 8F10C and 8F10D showed only weak binding to the complex. These results suggest that antibodies 7E3 and 8F10B are directed towards cryptic epitopes exposed on gp120 in response to sCD4 and SC binding.

Immunological Response Against gp120-CD4 Complex In Goats

Figure 6:
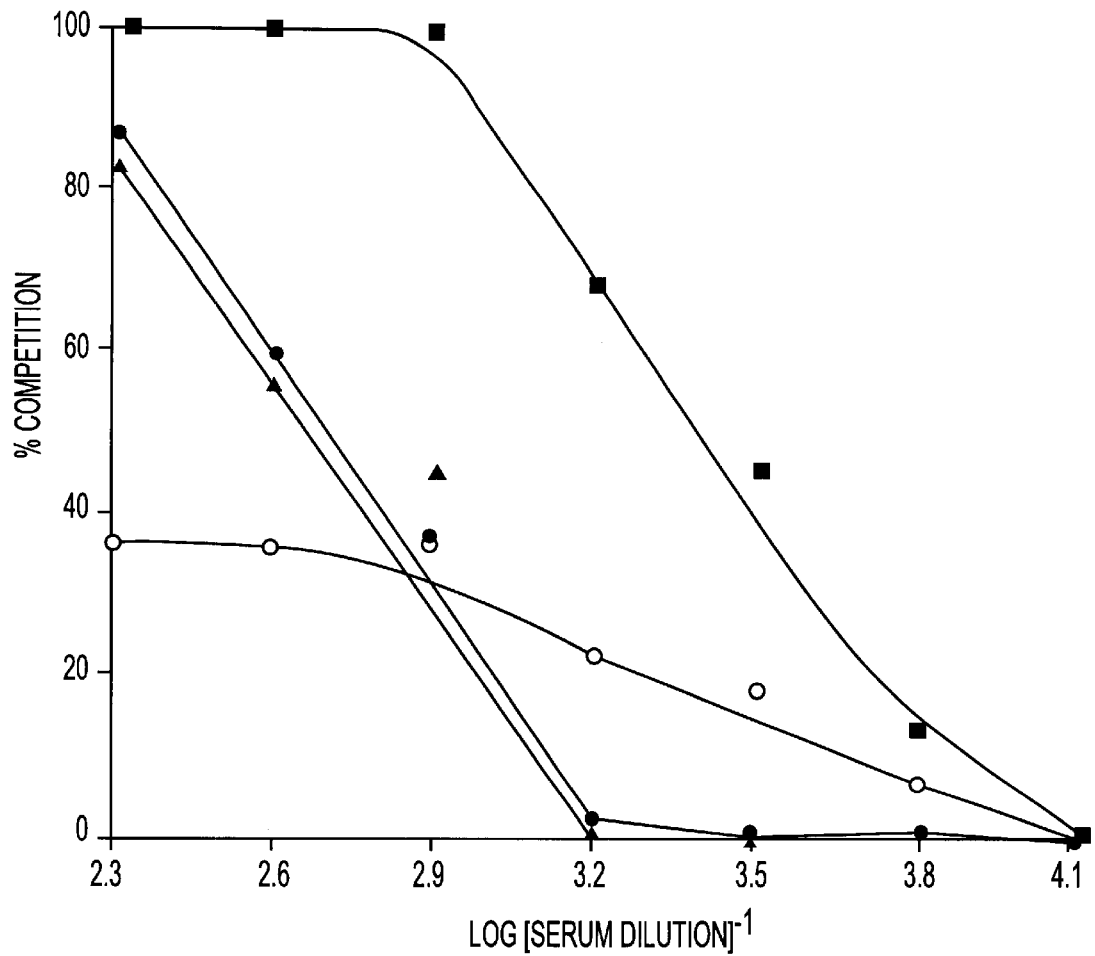
FIG. 6 is a graph showing competitive ELISA with complex-specific monoclonal antibodies and immune goat serum. Limiting dilutions of purified MoAb 7E3 (■), MoAb 8F10B(○), MoAb 8F10C(●) and MoAb 8F10D (▲) were incubated with serial dilutions of goat 69 serum and tested in go120-CD4 ELISA. Percent competition was calculated as level of antibody binding in immune serum versus binding in prebleed serum.
Figure 7:
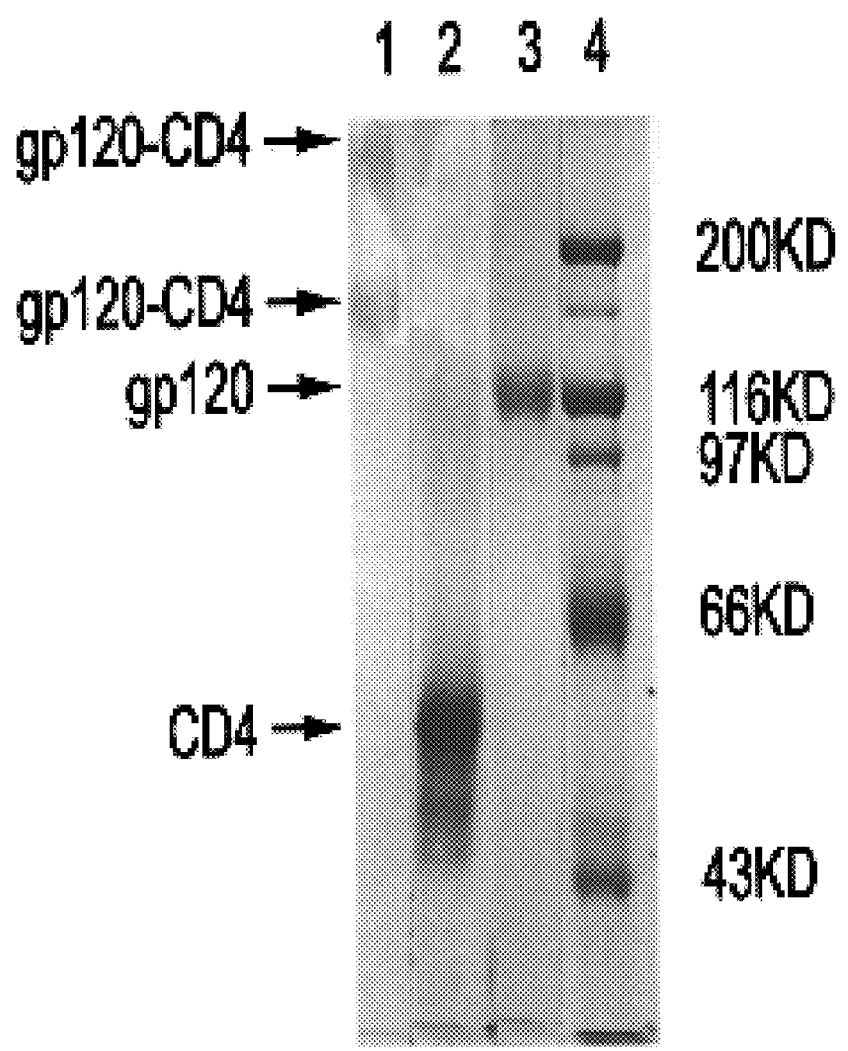
FIG. 7 is a photograph of a gel showing gp120-CD4 complexes prepared according to Example III.

We have also analyzed the immunogenic response against gp120-CD4 complex in a larger species of animals. An animal (goat 69) was repeatedly inoculated with 100 µg gp120-CD4 complex in Freund's adjuvant and after the fifth inoculation the serum was examined by ELISA for reactivity with gp120, sCD4 and the complex. Antibodies reactive against both free gp120 and sCD4 were detected in the sera. To determine if complex-specific antibodies were also elicited, the serum was tested in cross-competition assays with MoAbs 7E3, 8F10B, 8F10C, and 8F10D. Two-fold serial dilutions of goat 69 serum were incubated with limiting dilutions of each MoAb and tested in gp120-CD4 complex ELISA. As shown in FIG. 6, antibodies in the goat serum were able to block the binding of all four monoclonal antibodies.

The goat serum was tested for neutralizing antibodies in syncytium blocking and cell-free infection assays (Table 3). For comparison, serum from another animal (goat 58) taken after five inoculations with HIV-1$_{IIIE}$ viral gp120, was also tested. In syncytium assays, goat 69 serum reduced syncytium formation ≦80% at titers of 1:640 and 1:80 against HIV-1IIIB and HIV-1MN, respectively; goat 58 serum was much less effective. Goat 69 serum neutralized cell-free infection of CEM cells by HIV-1IIIB with a titer of 1:80. Again, this titer was significantly higher than the titer (1:20) of goat 58 serum. Goat 69 serum also mediated group-specific neutralization of cell-free infection by primary isolates HIV-1MN and HIV-1JRFL (Table 3). The neutralizing titer (1:80) was comparable to that of a broadly neutralizing human serum (1:160) tested in parallel; goat 58 serum failed to block HIV-1MN infection even at <1:20 dilution. Goat 69 serum was retested after removal of anti-CD4 antibodies by preabsorption with CEM cells. Removal of such antibodies was verified by flow cytometric analysis with SupT1 cells which showed nearly 90% reduction in cell surface binding. Despite this reduction, the neutralization titer of the absorbed serum was only two-fold less (1:40) than unabsorbed serum, indicating that neutralization is not entirely due to anti-CD4 antibodies.

The results presented in this example indicate that covalently cross-linked gp120-CD4 complexes possess a number of immunogenic complex-specific epitopes. At least a portion of these epitopes reside on the gp120 moiety of the complex. Moreover, some complex-specific epitopes are targets for broadly neutralizing antibodies specifically effective against cell-free infection by diverse HIV-1 strains, including primary field isolates targeted toward PBMC. Based on these findings, it is possible that the complexes could serve as a protective vaccine or immunotherapeutic reagent.

Example III

Preparation Of gp120-CD4 Complex (1:1 Molar Ratio) Free From Any Uncomplexed CD4

Figure 4A:
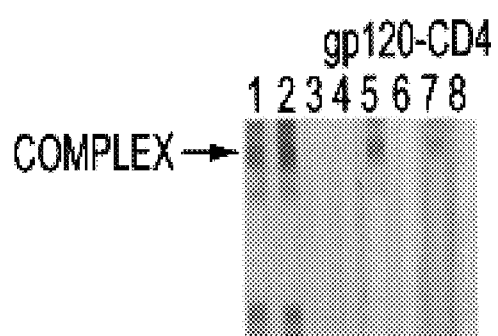
FIG. 4 shows Western blot assays of monoclonal antibodies raised against gp120-CD4 complexes with gp120, sCD4 and complex. Lane 1 is MoAb7E3, lane 2 is MoAb 8F10B, lane 3 is MoAb 8F10C, lane 4 is MoAb 8F10D, lane 5 is anti-gp120 MoAb, lane 6 is anti-p24 MoAb (negative control), lane 7 is rabbit anti-CD4 hyperimmune serum, and lane 8 is normal rabbit serum.
Figure 4B:
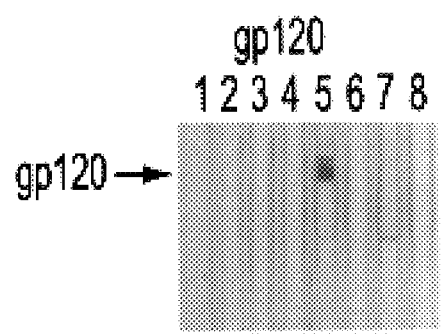
Figure 4C:
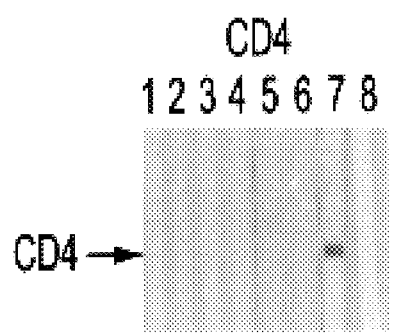

In the immunization protocol described above gp120 and CD4 were complexed at a 1:2 molar ratio. As the immunization with this material resulted in the isolation of anti-CD4 antibodies, we wanted to prepare gp120-CD4 complex (1:1 molar ratio) free from any uncomplexed receptor molecules to optimize the conditions for eliciting anti-gp120 antibodies. gp120 and CD4 (1:1 molar ratio) were bound at 37° C. for 1 hr, reacted with BS for 1 hr at room temperature and then overnight at 4° C. After blocking the free crosslinker with Tris buffer (pH 8.0), the solution was treated with Sepharose coupled to anti-CD4 monoclonal antibody E for 30 min at room temperature. As E binds to an epitope on CD4 involved in the interaction with gp120, this treatment removed any uncomplexed CD4 present. A gel showing gp120-CD4 complex prepared in this manner is shown in FIG. 4. It was clear that only the complex with molecular weight 170 kD and ~340 kD is evident in the gel. There was no free gp120 or CD4 present in the preparation.

Example IV

In order to more accurately determine if the immune response to gp120-CD4 complexes differs from the responses to the individual complex components, the following experiment was conducted. Separate groups of mice were inoculated witn equal amounts of CD4, gp120 or gp120-CD4 complexes. After five inoculations, sera were taken from the animals and analyzed. As shown in Table 4, all three of the CD4-immunized animals possessed syncytium blocking seroantibodies effective against HIV1$_{IIIB}$ and HIV-1$_{MN}$. All four sera from the complex-immunized animals blocked HIV-1$_{IIIB}$ induced syncytia; two of the four also blocked syncytia induced by HIV-1$_{MN}$. Overall, neutralizing titers in sera from complex-immunized animals was lower than sera from CD4-immunized animals. Surprisingly, none of the gp120-immunized animals displayed syncytium blocking seroantibodies.

Reactivity with CD4 in ELISA between the CD4-immunized and complex-immunized groups was similar (Table 4). The one exception was a complex-immunized animal (mouse 8) which possessed a titer of anti-CD4 antibodies significantly lower than the other animals. Among complex-immunized animals, the level of anti-CD4 reactivity did not correlate with syncytium blocking activity; mouse 10 serum was more effective in blocking syncytia than mouse 9 serum, even though mouse 9 serum had a slightly higher level of anti-CD4 reactivity.

Overall, complex-immunized animals possessed lower titers of anti-V3 loop antibodies; such antibodies were virtually absent from mouse 9 serum.

Example V

Sera from CD4-immunized and complex-immunized animals were also tested for reactivity with a variety of synthetic peptides derived from the CD4 sequence (Table 5). Although the overall level of anti-CD4 reactivity between CD4-immunized and complex-immunized groups was similar (Table 4), the patterns of reactivity with linear epitopes differed. While sera from CD4-immunized animals reacted with peptides derived from the N-terminal portion of CD4 (peptides A and B), such reactivity was absent in sera from complex-immunized animals. This is in accordance with the fact that the N-terminus of CD4 reacts with gp120. The prevalence of reactivity with a peptide derived from domain 3 of CD4 (peptide D) was also reduced among complex-immunized animals relative to CD4-immunized animals. Notably, reactivicy with a peptide derived from domain 4 of CD4 (peptide F) was unique to complex-immunized animals 10 and 11.

The data of Examples IV and V, taken together, indicate that the immune response against gp120-CD4 complexes is unique and different from responses to free CD4 and free gp120. Differences in the anti-complex response are reflected in 1) a reduced response against the gp120 V3 loop; 2) a reduced response against linear epitopes in the CD4 N-terminus; 3) an increased response to linear epitopes in CD4 domain 4. It should be noted that the latter epitopes may be hidden in the free CD4 molecule.

According to the present invention, using gp120-sCD4 complexes as immunogens, we have been able to raise HIV-1 neutralizing antibodies that are complex specific. The results we have obtained with these antibodies show that covalently coupled gp120-CD4 complexes possess immunogenic epitopes that are not normally functional in the unbound proteins.

TABLE 1

Reactivity of Monoclonal Antibodies Raised Against gp120-DC4 Complexes in ELISA

| | | (OD 450 nm) | | |
|---|---|---|---|---|
| Antibody | Isotype | CD4 | gp120 | Complex |
| 7E3 | IgA | .427 | .340 | >3.0 |
| 8F10B | IgG$_1$ | .146 | .175 | 1.5 |
| 8F10C | IgG$_1$ | .119 | .191 | >3.0 |
| 8F10D | IgG$_1$ | .208 | .202 | >3.0 |
| anti-gp120 | IgG$_1$ | .088 | >2.0 | >2.0 |
| anti-CD4 | IgG$_1$ | >3.0 | .103 | >3.0 |

The results shown are with hybridoma supernatants, the a same specificities were evident with purified immunoglobulin.

TABLE 2

Neutralization of Cell-Free HIV-1IIIB and of HIV-1MN Primary Isolate by gp120-CD4 Complex-Specific Monoclonal Antibodies

| Antibody Concentration | | % Inhibition[a] | |
|---|---|---|---|
| µg/ml | | HIV-1$_{IIIB}$ | HIV-1$_{MN}$ |
| 7E3 | 100 | 37 | 88.7 |
| | 50 | 55 | 69.8 |
| | 25 | 0 | 29.8 |
| 8F10B | 100 | 26.2 | 67.2 |
| | 50 | 6.2 | 36.3 |
| | 25 | 0 | 28 |
| 8F10C | 100 | 0 | 75.8 |
| | 50 | 0 | 29 |
| | 25 | 0 | 0 |
| 8F10D | 100 | 17 | 0 |
| Anti-CD4 (control) | 50 | 100 | 100 | aPHA stimulated PBMC (2×10$^5$ cells) were infected with either HIV-1IIIB or a primary isolate of HIV-1MN (50 TCID50Y for 18 hr in the presence of the indicated amounts of purified antibodies. Cells were then washed and cultured in fresh medium containing the same quantities of antibodies. The p24 content of the supernatant was determined on day 7 and the percent inhibition was calculated relative to control assays carried out in the absence of the antibodies.

TABLE 3

Neutralizing Activity of Sera from Goats Immunized with Either gp120-CD4 Complex or gp120

| | | Syncytium Blocking[a] HIV-1 Strain | | Cell-Free Neutralization[b] HIV-1 Strain/Target Cell | | |
|---|---|---|---|---|---|---|
| Serum | Immunogen | IIIB | MN | IIIB/CEM | NM/PBMC | JRFL/PBMC |
| Goat 69 | gp120-CD4 Complex | 1:640 | 1:80 | 1:80 | 1:80 | 1:80 |
| Goat 58 | gp120 | 1:20 | <1:20 | 1:20 | <1:20 | Not tested |
| Goat 69 (Cell Absorbed) | gp12p-CD4 Complex | <1:25 | <1.25 | Not tested | 1:40 | Not tested |

[a]HIV-1$_{IIIB}$-infected H9 cells were incubated with uninfected CEM cells in the presence of two-fold serial dilutions of each serum. The number of syncytia were scored in 3 fields of each well after 24 hr.
[b]Immune and preimmune serum from each goat was diluted 1:10 in culture media. The immune serum was then diluted serially in preimmune serum, thus maintaining a constant serum concentration in all assay wells. Preimmune goat sera and normal human serum did not demonstrate neutralization relative to control assays in which serum was omitted.
The titers shown produced ≥ 80% reaction in syncytia or neutralization relative to matched preimmune sera.

TABLE 4

| Mouse | Immunogen | Syncytia Blocking Titer[a] HIV-1$_{IIIB}$/HIV-1$_{MN}$ | HIV-1$_{B10}$$^{V3}$ Peptide ELISA Titer[b] | CD4 ELISA Titer[c] |
|---|---|---|---|---|
| 1 | CD4 | 1:1600/1:1600 | Not Tested | >1:256,000 |
| 2 | CD4 | 1:800/1:1600 | Not Tested | >1:256,000 |
| 3 | CD4 | 1:800/1:400 | Not Tested | >1:256,000 |
| 4 | gp120 | <1:50/<1:50 | 1:3200 | Not Tested |
| 5 | gp120 | <1:50/<1:50 | 1:1600 | Not Tested |
| 6 | gp120 | <1:50/<1:50 | 1:200 | Not Tested |
| 7 | gp120 | <1:50/<1:50 | 1:3200 | Not Tested |
| 8 | complex | 1:100/<1:50 | 1:400 | 1:32,000 |
| 9 | complex | 1:100/<1:50 | <1:25 | 1:256,000 |
| 10 | complex | 1:400/1:200 | 1:800 | 1:128,000 |
| 11 | complex | 1:400/1:100 | 1:800 | 1:128,000 |

[a]Titers are given as the highest serum dilution producing 100% blocking of syncytia formation. Preimmune sera did not reduce syncytia relative to control experiments in which serum was absent.
[b]Serial two-fold dilutions of each serum was tested. ELISA valves (absorbance at 450 nm) were converted by subtraction of valves obtained with the same dilutions of preimmune serum. Titers are given as the highest serum dilution having a corrected ELISA valve of $\leq 0.5$.
[c]Titers are given as the highest serum dilution having a converted ELISA valve of $\leq 0.5$.

TABLE 5

| | | CDR4 Peptide ELISA Valves ($A_{450nm}$)[a] | | | | | | | | | |
|---|---|---|---|---|---|---|---|---|---|---|---|
| Mouse | Immunogen | A | B | C | D | E | F | G | H | I | J | K |
| 1 | CD4 | 1.58 | 1.05 | 0.16 | 2.65 | 0.21 | 0.18 | 0.35 | 0.21 | 0.13 | 0.15 | 0.19 |
| 2 | CD4 | 2.37 | 0.38 | 0.17 | 2.6 | 0.22 | 0.17 | 0.14 | 0.21 | 0.15 | 0.18 | 0.24 |
| 3 | CD4 | 0.56 | 0.29 | 0.12 | 2.34 | 0.18 | 0.13 | 0.21 | 0.19 | 0.13 | 0.14 | 0.20 |
| 8 | Complex | 0.28 | 0.27 | 0.17 | 0.40 | 0.23 | 0.16 | 0.13 | 0.19 | 0.15 | 0.16 | 0.26 |
| 9 | Complex | 0.23 | 0.29 | 0.20 | 0.23 | 0.21 | 0.19 | 0.15 | 0.20 | 0.14 | 0.24 | 0.17 |
| 10 | Complex | 0.17 | 0.33 | 0.26 | 0.61 | 0.3 | 1.53 | 0.17 | 0.36 | 0.17 | 0.35 | 0.13 |
| 11 | Complex | 0.33 | 0.43 | 0.3 | 2.2 | 0.36 | 0.56 | 0.34 | 0.36 | 0.28 | 0.3 | 0.20 |

[a]Sera were tested at a dilution of 1:1000 for reactivity with peptides derived from the CD4 sequence. Peptide A, residues 25–58; B, residues 37–53; C, Residues 318–335; D, residues 230–249; E, residues 297–314; F, residues 330–344; G, residues 350–369; H, residues 310–324; I, residues 81–92 (Benzylated); J, residues 81–92; K, irrelevant peptide. ELISA valves $\geq$ two-fold higher than valves with irrelevant peptide are shown in Bold type. Reactivity of preimmune serum with the CD4 peptides was the same as with the irrelevant peptide.

REFERENCES

1. Watanabe, M., Chen, Z. W., Tsubota, H., Lord, C. I., Levine, C. G. and Letvin, N. L. Soluble human CD4 elicits an antibody response in rhesus monkeys that inhibits simian immunodeficiency virus replication. Proc. Natl. Acad. Sci. USA 88:120–124, 1991.
2. Sattentau, Q. J. and Moore, J. P. Conformational changes induced in the human immunodeficiency virus envelope glycoprotein by soluble CD4 binding. J. Exp. Med. 174:407–415, 1991.
3. Robert-Guroff, M. HIV-neutralizing antibodies: epitope identification and significance for future vaccine. Int. Rev. Immunol. 7:15–30, 1990.
4. Putney, S. How antibodies block HIV infection: paths to an AIDS vaccine. TIBS 17:1991–196, 1992.
5. Putney, S. D., Rusche, J., Javaherian, K., Matthews, T. and Bolognesi, D. Structural and functional features of the HIV envelope glycoprotein and considerations for vaccine development. Biotechnology 14:81–110, 1990.
6. Allan, J. S., Coligan, J. E., Barin, F., McLane, M. F., Sodroski, J. G., Rosen, C. A., Haseltine, W. A., Lee, T. H. and Essex, M. Major glycoprotein antigens that induce antibodies in AIDS patients are encoded by HTLV-III. Science 228:1091–1094, 1985.
7. Veronese, F. D., DeVico, A. L., Copeland, T. D., Oroszlan, S., Gallo, R. C. and Sarngadharan, M. G. Characterization of gp41 as the transmembrane protein coded by the HTLV-III/LAV envelope gene. Science 229:1402–1405, 1985.
8. Ohno, T., Terada, M., Yoneda, Y., Shea, K. W., Chambers, R. F., Stroka, D. M., Nakamura, M. and Kufe, D. W. A broadly neutralizing monoclonal antibody that recognizes the V3 region of human immunodeficiency virus type 1 glycoprotein gp120. Proc. Natl. Acad. Sci. USA 88:10726–10729, 1991.
9. Masuda, T., Matsushita, S., Kuroda, M. J., Kannagi, M., Takatsuki, K. and Harada, S. Generation of neutralization-resistant HIV-1 in vitro due to amino acid interchanges of third hypervariable env region. J. Immunol. 145:3240–3246, 1990.
10. Ho, D. D., Kaplan, J. C., Rackauskas, I. E. and Gurney, M. E. Second conserved domain of gp120 is important for HIV infectivity and antibody neutralization. Science 239:1021–1023, 1988.
11. Sun, N. C., Ho, D. D., Sun, C. R., Liou, R. S., Gordon, W., Fung, M. S., Li, X. L., Ting, R. C., Lee, T. H., Chang, N. T. and Chang, T. W. Generation and characterization of monoclonal antibodies to the putative CD4-binding domain of human immunodeficiency virus type 1 gp120. J. Virol. 63:3579–3585, 1989.
12. Chanh, T. C., Dreesman, G. R., Kanda, P., Linette, G. P., Sparrow, J. T., Ho, D. D. and Kennedy, R. C. Induction of anti-HIV neutralizing antibodies by synthetic peptides. EMBO J. 5:3065–3071, 1986.
13. Ho, D. D., McKeating, J. A., Li, X. L., Moudgil, T., Daar, E. S., Sun, N. C. and Robinson, J. E. Conformational epitope on gp120 important in CD4 binding and human immunodeficiency virus type 1 neutralization identified by a human monoclonal antibody. J. Virol. 65:489–493, 1991.
14. Dalgleish, A. G., Beverley, P. C., Clapham, P. R., Crawford, D. H., Greaves, M. F. and Weiss, R. A. The CD4 (T4) antigen is an essential component of the receptor for the AIDS retrovirus. Nature 312:763–767, 1984.
15. McDougal, J. S., Kennedy, M. S., Sligh, J. M., Cort, S. P., Mawle, A. and Nicholson, J. K. Binding of HTLV-III/LAV to T4+T cells by a complex of the 110K viral protein and the T4 molecule. Science 231:382–385, 1986.
16. Thali, M., Furman, C., Ho, D. D., Robinson, J., Tilley, S., Pinter, A., and Sodroski, J. Discontinuous, conserved neutralization of epitopes overlapping the CD4-binding region of human immunodeficiency virus type 1 gp120 envelope glycoprotein. J. Virol. 66:5635–5641, 1992.

17. Moore, J. P., McKeating, J. A., Weiss, R. A. and Sattentau, Q. J. Dissociation of gp120 from HIV-1 virions induced by soluble CD4. Science 250:1139–1142, 1990.
18. Hart, T. K., Kirsh, R., Ellens, H., Sweet, R. W., Lambert, D. M., Petteway, S. R., Jr., Leary, J. and Bugelski, P. J. Binding of soluble CD4 proteins to human immunodeficiency virus type 1 and infected cells induces release of envelope glycoprotein gp120. Proc. Natl. Acad. Sci. USA 88:2189–2193, 1991.
19. Mizuochi, T., Matthews, T. J., Kato, M., Hamako, J., Titani, K., Solomon, J. and Feizi, T. Diversity of oligosaccharide structures on the envelope glycoprotein. gp 120 of human immunodeficiency virus 1 from the lymphoblastoid cell line H9. Presence of complex-type oligosaccharides with bisecting N-acetylglucosamine residues. J. Biol. Chem. 265:8519–8524, 1990.
20. Geyer, H., Holschbach, C., Hunsmann, G. and Schneider, J. Carbohydrates of human immunodeficiency virus. Structures of oligosaccharides linked to the envelope glycoprotein 120. J. Biol. Chem. 263:11760–11767, 1988.
21. Larkin, M., Childs, R. A., Matthews, T. J., Thiel, S., Mizuochi, T., Lawson, A. M., Savill, J. S., Haslett, C., Diaz, R. and Feizi, T. Oligosaccharide-mediated interactions of the envelope glycoprotein gp120 of HIV-1 that are independent of CD4 recognition. AIDS 3:793–798, 1989.
22. Ezekowitz, R. A., Kuhlman, M., Groopman, J. E. and Byrn, R. A. A human serum mannose-binding protein inhibits in vitro infection by the human immunodeficiency virus. J. Exp. Med. 169:185–196, 1989.
23. Schooley, R. T., Merigan, T. C., Gaut, P., Hirsch, M. S., Holodniy, M., Flynn, T., Liu, S., Byington, R. E., Henochowicz, S., Gubish, E. and et al, Recombinant soluble CD4 therapy in patients with the acquired immunodeficiency syndrome (AIDS) and AIDS-related complex. A phase I–II escalating dosage trial. Ann. Intern. Med. 112:247–253, 1990.
24. Kahn, J. O., Allan, J. D., Hodges, T. L., Kaplan, L. D., Arri, C. J., Fitch, H. F., Izu, A. E., Mordenti, J., Sherwin, J. E., Groopman, J. E. and et al, The safety and pharmacokinetics of recombinant soluble CD4 (rCD4) in subjects with the acquired immunodeficiency syndrome (AIDS) and AIDS-related complex. A phase 1 study. Ann. Intern. Med. 112:254–261, 1990.
25. Watanabe, M., Boyson, J. E., Lord, C. I. and Letvin, N. L. Chimpanzees immunized with recombinant soluble CD4 develop anti- self CD4 antibody responses with anti-human immunodeficiency virus activity. Proc. Natl. Acad. Sci. USA 89:5103–5107, 1992.
26. Grewe, C., Beck, A., and Gelderblom, H. R. HIV: Early virus-cell interactions. J. Acq. Immune Def. Synd. 3:965–974, 1990.
27. Robinson, W. E., Jr., Montefiori, D. C. and Mitchell, W. M. Evidence that mannosyl residues are involved in human immunodeficiency virus type 1 (HIV-1) pathogenesis. AIDS Res. Hum. Retroviruses 3:265–282, 1987.
28. Gattegno, L., Ramdani, A., Jouault, T., Saffar, L. and Gluckman, J. C. Lectin-carbohydrate interactions and infectivity of human immunodeficiency virus type 1 (HIV-1). AIDS Res. Hum. Retroviruses 8:27–37, 1992.
29. Pal, R. Veronese, F. D., Nair, B. C., Rahman, R., Hoke, G., Mumbauer, S. W., and Sarngadharan, M. G. Characterization of a neutralizing monoclonal antibody to the external glycoprotein of HIV-1. Intervirology, 86, 86–93 (1992).
30. Veronese, F. D., Rahman, R., Pal, R., Boyer, C., Romano, J., Kalyanaraman, V. S., Nair, B. C., Gallo, R. C. and Sarngadharan, M. G. Delineation of immunoreactive, conserved regions in the external glycoprotein of the human immunodeficiency virus type 1. AIDS Res. Human Retroviruses 8:1125–1132, 1992.
31. Celada, F., Cambiaggi, C., Maccari, J., Burastero, S., Gregory, T., Patzer, E., Porter, J., McDanal, C. and Matthews, T. Antibody Raised against Soluble CD4-rgp120 complex recognizes the CD4 moiety and blocks membrane fusion without inhibiting CD4-gp120 binding. J. Exp. Med., 172:1143–1150, 1990.
32. Gershoni, J. M., Denisova, G., Raviv, D., Smorodinski, N. I. and Buyaner, D. HIV binding to its receptor creates specific epitopes for the CD4/gp120 complex. FASEB J. 7:1185–1187, 1993.
33. Pal, R., DeVico, A., Rittenhouse, S. and Sarngadharan, M. G. Conformational perturbation of the envelope glycoprotein gp120 of human immunodeficiency Virus type 1 by soluble CD4 and the lectin succinyl ConA. Virology 194:833–837, 1993.

We claim:

1. A method of raising neutralizing antibodies against HIV, comprising administering to a subject an immunogenically effective amount of a complex of gp120 covalently bonded to CD4 in a pharmaceutically acceptable carrier.

2. A method of raising neutralizing antibodies against HIV, comprising administering to a subject an immunogenically effective amount of a complex of gp120 covalently bonded to succinyl concanavalin A in a pharmaceutically acceptable carrier.

* * * * *